United States Patent [19]

Burdet et al.

[11] Patent Number: 5,681,977
[45] Date of Patent: Oct. 28, 1997

[54] METHOD FOR THE PRODUCTION OF (3-ALKOXYCARBONYL-2-BUTENYL) TRIPHENYLPHOSPHONIUM SALTS

[75] Inventors: Bruno Burdet, Baldersheim, France; August Rüttimann, Arlesheim, Switzerland; Jean-Marie Santer, St. Louis, France; Theodor Siegfried, Riehen, Switzerland

[73] Assignee: Roche Vitamins Inc., Paramus, N.J.

[21] Appl. No.: 779,785

[22] Filed: Jan. 7, 1997

Related U.S. Application Data

[62] Division of Ser. No. 558,993, Nov. 16, 1995, Pat. No. 5,631,398, which is a division of Ser. No. 405,682, Mar. 17, 1995, Pat. No. 5,502,236.

[30] Foreign Application Priority Data

Mar. 23, 1994 [CH]  Switzerland ................. 868/94

[51] Int. Cl.$^6$ ........................... C07C 303/06
[52] U.S. Cl. ........................................... 558/22
[58] Field of Search ................................ 558/22

[56] References Cited

U.S. PATENT DOCUMENTS

| 4,937,308 | 6/1990 | Knaus et al. | 558/124 |
| 5,021,587 | 6/1991 | Mathew | 548/543 |
| 5,161,566 | 11/1992 | Mathew | 137/328 |
| 5,502,236 | 3/1996 | Burdet et al. | 558/460 |

FOREIGN PATENT DOCUMENTS 3244273   5/1984   Germany.

OTHER PUBLICATIONS

Nurrenbach, et al, Oxidation von Phosphor–Yliden mit Hydroperoxiden Ein neuer und ergiebiger Weg zu symmetrischen Cartinoiden, Liebigs Ann. Chem. pp. 1146–1159 (1977).

Yoshihara, et al, Chemical Abstracts, vol. 119, No. 21, 22, Abstract No. 225949 (1993).

*Primary Examiner*—Joseph McKane
*Attorney, Agent, or Firm*—George W. Johnston; Dennis P. Tramaloni; Bruce A. Pokras

[57] ABSTRACT

Novel processes and intermediates useful for the manufacture of the Wittig ester salts are disclosed. The Wittig ester salts are known as important $C_5$ building blocks for the manufacture of various polyenecarboxylic acid esters in the field of carotenoid chemistry.

6 Claims, No Drawings

METHOD FOR THE PRODUCTION OF (3-ALKOXYCARBONYL-2-BUTENYL) TRIPHENYLPHOSPHONIUM SALTS

This is a division of application Ser. No. 08/558,993, filed Nov. 16, 1995, now U.S. Pat. No. 5,631,398 which is a Division of Ser. No. 08/405,682, filed Mar. 17, 1995, now U.S. Pat. No. 5,502,236.

BACKGROUND OF THE INVENTION

The present invention is concerned with a novel process for the manufacture of a Wittig ester salt, especially of a (3-alkoxycarbonyl-2-butenyl)triphenylphosphonium chloride or ethyl sulphate, each of which is known as an important $C_5$ building block for the manufacture of various polyenecarboxylic acid esters in the field of carotenoid chemistry.

The phosphonium salt 3-ethoxycarbonyl-2-butenyltriphenylphosphonium chloride can be manufactured readily, as is known, from ethyl γ-chloro-tiglate by reaction with triphenylphosphine in toluene at about 110° C. [Nürrenbach et al., Liebigs Ann. Chem. 1977, 1146–1159]. Ethyl γ-chloro-tiglate itself and other lower alkyl γ-halo-tiglates can be produced according to various known methods, for example:

from the alkyl tiglate by Ziegler bromination (using N-bromosuccinimide in carbon tetrachloride) [see Inhoffen et al., Liebigs Ann. Chem. 580, 1 (1953); Inhoffen et al., Liebigs Ann. Chem. 580, 7 (1953); as well as Korte et al., Chem. Ber. 89, 2675 (1956)]. However, Dreiding et al. [Helv. Chim. Acta 53, 383 (1970); see also Cozzi et al., Tetr. Lett. 31, 5661 (1990)] were able to show later that this bromination does not proceed regioselectively and always gives a mixture of the two alkyl γ-bromo-tiglate isomers (desired) and 2-alkoxycarbonyl-1-bromo-2-butene (byproduct), which are very difficult to separate from one another;

from an alkyl pyruvate by reaction with vinylmagnesium chloride (or with bromomagnesium acetylide and subsequent partial hydrogenation) followed by an allyl rearrangement with thionyl chloride (Nürrenbach et al., ibid.) or a phosphorus trihalide [Kitahara et al., Tetrahedron 44, 4713 (1988)]. These methods are, however, expensive and uninteresting from the industrial point of view;

by means of a Wittig reaction of the triphenyl(Ph) phosphorane $Ph_3P=C(CH_3)COOC_2H_5$ with chloroacetaldehyde [Albertson et al., J. Med. Chem. 20, 602 (1977) as well as Stotter et al., Tetr. Lett. 1975, 1679]. This method is also expensive and uninteresting from the industrial point of view;

starting from 2-methyl-3-butenenitrile by ethanolysis, halogenation and subsequent dehydrohalogenation (German Offenlegungsschrift 3,244,273 as well as U.S. Pat. No. 4,937,308). This method has also been found to be relatively expensive and, moreover, gives unsatisfactory results; and by reacting methyl vinyl ketone with hydrocyanic acid, subsequently converting the thus-obtained nitrile into an ester (Pinner reaction) and subjecting the latter to allyl rearrangement with thionyl chloride or another halogenating agent (German Offenlegungsschrift 2,852,343 and Nürrenbach et al., ibid). The disadvantage of this method is, inter alia, the use of the highly toxic reagents hydrocyanic acid, thionyl chloride and methyl vinyl ketone.

SUMMARY OF THE INVENTION

The object of the present invention is to manufacture a (3-alkoxycarbonyl-2-butenyl) triphenylphosphonium chloride and the corresponding ethyl sulphate in an economical manner, inter alia using as few process steps as possible, starting from a readily accessible starting material and avoiding as far as possible the aforementioned disadvantages of the state of the art.

The process in accordance with the invention for the manufacture of a (3-alkoxycarbonyl-2-butenyl) triphenylphosphonium chloride or ethyl sulphate of the formula:

$$X^-\text{---}(C_6H_5)_3P^+CH_2CH=C(CH_3)COOR \qquad I$$

wherein R is an alkyl group and X- is the chloride or ethyl sulphate ion (Cl— or $C_2H_5OSO_2O$—), comprises α-chlorinating 2-methyl-3-butenenitrile which has the formula:

$$CH_2=CHCH(CH_3)CN \qquad II$$

by reacting II with an alkali metal or alkaline earth metal hypochlorite to obtain the α-chlorinated compound 2-chloro-2-methyl-3-butenenitrile of the formula:

$$CH_2=CHC(Cl)(CH_3)CN \qquad III$$

then, in the first embodiment of the invention (Scheme 1), subjecting III to an alkanolysis by reacting III with an alkanol, ROH, wherein R is $C_{1-4}$-alkyl, to give the corresponding alkyl 2-chloro-2-methyl-3-butenoate of the formula:

$$CH_2=CHC(Cl)(CH_3)COOR \qquad IV$$

and subsequently reacting IV with triphenylphosphine in an organic solvent by which the 2-chloro group is removed and the double bond is shifted so as to give the desired (3-alkoxycarbonyl-2-butenyl)triphenylphosphonium chloride of the formula:

$$Cl^-\text{---}(C_6H_5)_3P^+CH_2CH=C(CH_3)COOR \qquad I',$$

In another embodiment of the invention (Scheme 2), III is firstly reacted with triphenylphosphine in an organic solvent by which the 2-chloro group is removed and the double bond is shifted so as to give (3-cyano-2-butenyl) triphenylphosphonium chloride of the formula:

$$Cl^-\text{---}(C_6H_5)_3P^+CH_2CH=C(CH_3)CN \qquad V$$

and subsequently V is subjected to an alkanolysis by reacting V with the alkanol ROH, described above, in the presence of concentrated sulphuric acid to give the desired (3-alkoxycarbonyl-2-butenyl) triphenylphosphonium ethyl sulphate of the general formula $$C_2H_5OSO_2O^-\text{---}(C_6H_5)_3P^+CH_2CH=C(CH_3)COOR \qquad I''.$$

In the above definition of the process in accordance with the invention the term "alkyl group" (R) means especially a straight-chain or branched alkyl group which contains 1 to 4 carbon atoms. This alkyl group is preferably methyl or ethyl, especially ethyl.

The alkali metal or alkaline earth metal hypochlorite used in the first step of the process is preferably sodium, potassium or calcium hypochlorite.

The entire process in accordance with the invention can be represented schematically as follows:

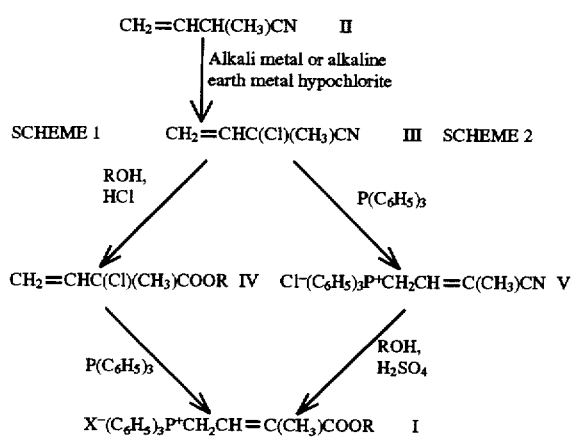

I': X—=Cl— (where II→III→IV→I': Scheme 1)
I": X—=C$_2$H$_5$OSO$_2$O— (where II→III→V—I": Scheme 2)

The starting material used in the process in accordance with the invention is the readily accessible and at the same time conveniently obtainable 2-methyl-3-butenenitrile II, which is a byproduct or waste product in adiponitrile production and which results by direct hydrocyanation of butadiene with cyanuric acid (see, for example, U.S. Pat. No. 3,850,973).

The 2-chloro-2-methyl-3-butenenitrile III produced from this starting material in the first step of the process in accordance with the invention as well as the intermediates produced in the next process step of each of Scheme 1 and Scheme 2 of the invention, namely the alkyl 2-chloro-2-methyl-3-butenoate IV and (3-cyano-2-butenyl) triphenylphosphonium chloride V, are, on the other hand, novel compounds. These novel compounds form a further aspect of the present invention.

It has been discovered in accordance with the invention that the reaction of 2-methyl-3-butenenitrile II with an alkali metal or alkaline earth metal hypochlorite surprisingly results in the α-chlorination of II to obtain 2-chloro-2-methyl-3-butenenitrile III. This α-chlorination is therefore one aspect of the present invention.

The α-chlorination method of the first process step of the invention is conveniently effected by any conventional means for chlorinating compounds using alkali metal or alkaline earth metal hypochlorites. The α-chlorination is preferably effected by reacting II with an aqueous solution of sodium, potassium or calcium hypochlorite. The reaction may be effected without a cosolvent, or, if desired, may be carried out in a mixture of the aqueous hypochlorite solution with an aprotic organic solvent which is essentially immiscible with water. This results in a two-phase solvent system. If the reaction is carried out in a two-phase solvent system, the reaction may be run without a catalyst or in the presence of a phase transfer catalyst. The method is preferably carried out at relatively low temperatures, i.e., room temperature or below.

As a source of hypochlorite, a commercial aqueous "Javelle water" (a liquid laundry bleach), which has a concentration of about 13% w/w (weight percent) of sodium hypochlorite, is an especially suitable aqueous sodium hypochlorite solution. Although concentrations lower than about 13 weight percent can be used, in the case of these lower concentrations an increasing tendency for the 2-methyl-3-butenenitrile II starting material to isomerize to 2-methyl-2-butenenitrile, which is inert to chlorination, is observed.

The best results are achieved with an aqueous sodium or potassium hypochlorite solution which has a hypochlorite concentration in the range of about 10 to about 20% w/w. When calcium hypochlorite is used as the chlorinating agent, a somewhat higher concentration range is preferred, namely from about 25 to about 35% w/w.

If the α-chlorination reaction is carried out in a two-phase solvent system, any conventional aprotic, water immisible organic solvent may be used. Art aliphatic ether, a lower, optionally halogenated alkane or a lower cycloalkane, in each case with up to 6 carbon atoms, or a petroleum ether, especially comes into consideration as the organic solvent. Preferred organic solvents are diethyl ether, diisopropyl ether, n-hexane, methylene chloride, carbon tetrachloride and cyclohexane.

If a two-phase solvent system is used, the α-chlorination reaction may be aided by the addition of a phase-transfer catalyst to the mixture of aqueous hypochlorite and aprotic organic solvent. Any conventional phase transfer catalysts may be used to aid the α-chlorination. The preferred phase transfer catalysts are quarternary ammonium salts, particularly, ALIQUAT 336 (methyltridecylammonium chloride), tetrabutylammonium bisulphate, benzyltributylammonium chloride, benzyltriethylammonium chloride, tetramethylammonium chloride and tetraethylammonium bromide, especially the ammonium salts having lower alkyl substituents such as, for example, tetramethylammonium chloride and tetraethylammonium bromide. When a catalyst is used, any amount sufficient to catalyze the phase transfer may be used, with about 2 to 5 mol % thereof based on the amount of starting material being preferred.

Any temperature sufficient to carry out the α-chlorination reaction may be used. The α-chlorination is preferably effected in the temperature range of about 0° C. to room temperature, particularly of about 5° to about 10° C. In general, the higher the reaction temperature, the faster the reaction is concluded. In the case of a reaction temperature of about 5° C., the conversion after five hours is only about 55%, while in the case of a reaction temperature of about 10° C., a conversion of about 90% is achieved after eight hours.

In accordance with the invention, the conversion of the α-chlorinated III to the final Wittig ester salt I my be accomplished by two schemes. Schemes 1 and 2, described above. In Scheme 1, the alkanolysis of 2-chloro-2-methyl-3-butenenitrile III to the alkyl 2-chloro-2-methyl-3-butenoate IV my be carried out by any conventional means. Preferrably this reaction is effected either by adding a solution of the 2-chloro-2-methyl-3-butenenitrile III in a suitable solvent to a previously produced solution of hydrogen chloride in an alkanol, or by introducing gaseous hydrogen chloride into a solution of the 2-chloro-2-methyl-3-butenenitrile III in an alkanol, which is optionally in admixture with a further solvent. Both alternatives may be carried out at any temperature sufficient to carry out the reaction., preferrably at temperatures in the range of about 0° C. to room temperature.

Any conventional solvent suitable for carrying out an alkanolysis may be used, in addition to the alkanol (in admixture therewith). Preferrably a lower aliphatic ether is used, e.g., diethyl ether or diisopropyl ether, with the volume ratio of alkanol:ether preferably being from about 5:1 to about 1:2, especially about 1:1. Other suitable solvents are lower alkanes, e.g., n-hexane, or lower cycloalkanes, e.g., cyclohexane, which was used as the solvent in the previous step. Other solvents, e.g., toluene, can be used, but appear to influence the conversion somewhat negatively.

With respect to the concentration of the hydrogen chloride in the alkanol or in the reaction medium, any concentration sufficient to carry out the alkanolysis reaction may be used. A concentration dose to the temperature-dependent saturation limit is preferred. In the case of the addition of a solution of hydrogen chloride in ethanol, the hydrogen chloride content of the ethanolic hydrogen chloride in the temperature range 0° to 20° C. is preferrably from about 47 to about 41%. In general, the yield of the alkyl 2-chloro-2-methyl-3-butenoate IV essentially increases with increasing hydrogen chloride concentration.

Moreover, the temperature of the reaction mixture at the beginning of the alkanolysis should preferrably not exceed about 10° C. in order to prevent an unnecessary loss of hydrogen chloride gas from the alkanolic phase. In the course of the reaction the temperature can then be increased successively, for example by about 2.5° C./hour, and the best yields appear to be realized at temperature of about 15° C. to about 17.5° C.

After completion of the alkanolysis reaction, the reaction mixture is hydrolyzed. The hydrolysis may be carried out by any conventional means, but is preferrably carried out by adding an ice/water mixture at about 0° C. to the reaction mixture, or vice-versa. During the addition, crystalline ammonium chloride normally precipitates from the alkanol phase and again passes completely into solution depending on the amount of water/ice which is added.

As will be evident from the above description of the reaction, under certain circumstances the crude product of the α-chlorination step can be reacted directly in the subsequent alkanolysis without separating the solvent, e.g., diethyl ether, diisopropyl ether, n-hexane or cyclohexane, used in the first process step, since the respective solvent can also be used in the second process step.

The last step of Scheme 1 is another aspect of the invention. In this step, the alkyl 2-chloro-2-methyl-3-butenoate IV is reacted with triphenylphosphine to obtain the phosphonium salt, (3-alkoxycarbonyl-2-butenyl) triphenylphosphonium chloride I'. In this reaction, the tertiary chlorine on the ester IV is removed and the double bond is shifted so as to obtain the desired (3-alkoxycarbonyl-2-butenyl) triphenylphosphoninm chloride I'. The reaction of the ester IV and the triphenylphosphine may be carried out under conditions known in the art for the preparation of Wittig salts. It is generally preferred that the reaction be carried out in an aprotic solvent and at elevated temperatures.

The reaction between the ester IV and the triphenylphosphine is preferably carried out in an aprotic organic solvent. Any conventional aprotic solvent may be used. The preferred solvents are a mononuclear aromatic solvent, e.g., benzene, toluene or a xylene, a dialkyl ketone, e.g., methyl isobutyl ketone, or an alkyl alkanoate, e.g., ethyl n-butyrate or ethyl isobutyrate.

The reaction between the ester IV and the triphenylphosphine is generally carried out at elevated temperature, e.g., in the temperature range of about 90° to about 150° C., preferably of about 110° to about 130° C., especially at the reflux temperature of the reaction mixture (e.g., at about 110° C. when toluene is used as the solvent).

The crude alkyl 2-chloro-2-methyl-3-butenoate IV from the previous step can be reacted with the triphenylphosphine without prior isolation. However, when a solvent other than those described above for the reaction of the ester IV with the triphenylphosphine, e.g., n-hexane, has been used in the preparation of the ester IV, this solvent should be replaced by a solvent described above, e.g., a mononuclear aromatic solvent such as toluene, which is suitable for the formation of the phosphonium salt. On the other hand, when the alkanol has been used as the sole solvent in the preparation of the ester IV, the ester IV can advantageously be extracted with the solvent to be used in the reaction of the ester IV with the triphenylphosphine in order thereby to avoid a solvent exchange.

Where, after carrying out the first and/or the second process step, it is desired to isolate and purify the respective product III or IV, then this can be effected in a manner known per se.

The sequence of reaction steps: α-chlorination, alkanolysis and phosphonium salt formation, described above represents Scheme 1 of the process in accordance with the invention. In Scheme 2, the last two process steps are in principle carried out in reverse sequence, whereby under the influence of the sulphuric acid in the alkanolysis the corresponding ethyl sulphate is obtained, however, instead of the phosphonium chloride.

The reaction of 2-chloro-2-methyl-3-butenenitrile III with triphenylphosphine involved in Scheme 2 of the process in accordance with the invention is carried out analogously to the phosphonium salt formation described in Scheme 1, i.e., in an aprotic organic solvent by which the 2-chloro group is removed and the double bond is shifted. The solvent is preferrably a mononuclear aromatic solvent, e.g., benzene; toluene or a xylene, a dialkyl ketone or an alkyl alkanoate. The reaction is carried out at elevated temperature such as, for example, in the temperature range of about 70° C. to about 130° C., preferably at the reflux temperature of the reaction mixture.

It has been discovered in accordance with the invention that the alkanolysis of (3-cyano-2-butenyl) triphenylphosphonium chloride V to obtain (3-alkoxycarbonyl-2-butenyl) triphenylphosphonium ethyl sulphate I" may be effected by reacting the phosphonium chloride V with an alkanol, ROH where R is $C_{1-4}$-alkyl, in the presence of sulphuric acid.

The alkanolysis of V to I" requires relatively drastic reaction conditions. The alkanolysis is effected in a mixture of the alkanol and concentrated, preferably 95 to 97%, sulphuric acid at an elevated temperature, preferably at the reflux temperature of the reaction mixture. The molar ratio of alkanol to sulphuric acid preferably is in the range of about 1:1 to about 3:1, and is especially about 2:1.

Where, after carrying out the first process step of Scheme 2, it is desired to isolate and purify the product III, then this can also be effected in a manner known per se. However, analogously to Scheme1, the crude product of the α-chlorination step can also be reacted directly with triphenylphosphine without separating the solvent, e.g., toluene, used in the first process step.

A further aspect of the process in accordance with the invention, Scheme 3, is a variation of Scheme 2 in that it ultimately produces I", and comprises proceeding from the starting material 2-methyl-3-butenenitrile II to the (3-cyano-2-butenyl)triphenylphosphonium chloride V via 3,4-dichloro-2-methylbutanenitrile [of the formula $ClCH_2CH(Cl)CH(CH_3)CN$ VI] and then 4-chloro-2-methyl-2-butenenitrile [of the for $ClCH_2CH=C(CH_3)CN$ VII]. The respective process comprises chlorinating 2-methyl-3-butenenitrile II with elementary chlorine to the dichloro compound 3,4-dichloro-2-methyl-butanenitrile VI, dehydrochlorinating VI using a base to obtain 4-chloro-2-methyl-2-butenenitrile VII, and then reacting VII with triphenylphosphine to give the desired (3-cyano-2-butenyl) triphenylphosphonium chloride V. 3,4-Dichloro-2-methylbutanenitrile VI is a novel compound, whereas 4-chloro-2-methyl-2-butenenitrile VII is a known compound

[see, for example, Lugtenburg et al., Recl. Tray. Chim. Pays-Bas, 109: 378 (1990)].

Scheme 3 may be shown schematically, as follows:

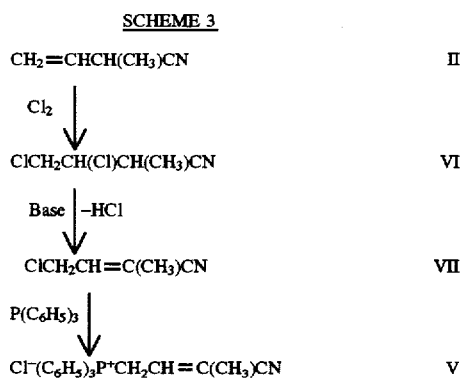

The chlorination of 2-methyl-3-butenenitrile II may be carried out by any conventional means. The chlorination is preferably carried out in a lower, optionally halogenated hydrocarbon as the solvent at low temperatures, especially below 0° C., and optionally in the presence of a base. Solvents which are preferred are alkanes with up to 6 carbon atoms, with n-pentane and n-hexane being, preferred, and halogenated alkanes, preferably chlorinated alkanes with up to six carbon atoms, with methylene chloride and carbon tetrachloride being preferred.

The temperature range in which the reaction is effected is preferably from about −80° C. to about +30° C., with a range of about −20° C. to about +20° C. being especially preferred. Where a base is used, this is preferably pyridine which, moreover, can serve as the solvent. It has been found to be advantageous to add the 2-methyl-3-butenenitrile II, optionally in solution in a part of the solvent used, to a solution of chlorine in the remaining solvent. However, the inverse addition (dropwise addition of the chlorine solution) can be carried out, which leads to similar results, or the chlorine can be introduced immediately into the solution of 2-methyl-3-butenenitrile II.

The subsequent dehydrochlorination may be carried out by any conventional means. Preferably this reaction is effected using an alkali metal alcoholate or hydroxide in a lower alcohol and/or in water. However, as an alternative, an optionally halogenated lower hydrocarbon of up to 6 carbon atoms, such as, for example, n-pentane, n-hexane or methylene chloride, or a mononuclear aromatic solvent, e.g., toluene, may be used as the solvent. A phase transfer catalyst is required when a halogenated hydrocarbon or a mononuclear aromatic is used. On the other hand, when n-pentane or n-hexane is used, the phase transfer catalyst is superfluous. Examples of phase transfer catalysts which can be used are those referred to above in connection with the α-chlorination of 2-methyl-3-butenenitrile II. Tetrabutylammonium chloride is especially preferred. The dehydrochlorination is preferably effected at temperatures between about −20° C. and about +40° C., with room temperature being especially preferred.

The last process step in Scheme 3, namely the reaction of the 4-chloro-2-methyl-2-butenenitrile VII with triphenylphosphine to obtain the (3-cyano-2-butenyl) triphenylphosphonium chloride V, may be effected by any conventional means. Preferably this reaction this reaction effected in a lower alkanol, e.g., isopropanol, as the solvent and at elevated temperature, preferably at the reflux temperature of the reaction mixture.

The (3-alkoxycarbonyl-2-butenyl)triphenylphosphonium chloride I' or ethyl sulphate I" manufactured in accordance with the invention can be used for the manufacture of various polyenecarboxylic acid esters by reaction with corresponding carbonyl compounds according to Wittig. Examples of various end products (alkyl polyenecarboxylates) are β-apo-8'-carotenoic acid alkyl ester [Guex et al., U.S. Pat. No. 3,113,961], β-apo-4'-carotenoic acid alkyl ester [neurosporaxanthin alkyl ester; Isler et al., Helv. Chim. Acta 42, 864 (1959)] and crocetin alkyl ester [Buchta et al., Chem. Ber. 93, 1349 (1960)].

The invention is illustrated on the basis of the following Examples.

EXAMPLE 1

Production of 2-chloro-2-methyl-3-butenenitrile 10 g (0.1 mmol) of 2-methyl-3-butenenitrile [about 85% pure according to gas chromatography (GC)] are added to a mixture of 100 ml of methylene chloride/50 ml of water and treated at room temperature with 100 ml of 10% Javelle water (about 0.15 mol), followed by 3 g (10 mol %) of tetrabutylammonium hydrogen sulphate. The reaction mixture is stirred at room temperature for 16 hours and thereafter subjected to a conventional working up. According to GC the isolated crude product consists to 56% of 2-chloro-2-methyl-3-butenenitrile and to 19% of 2-methyl-2-butenenitrile.

The crude product is distilled at 67° C./80 mm Hg on a small Vigreux column and the first fraction (5.4 g) is chromatographed on 250 g of silica gel (∅ 0.04–0.063) using n-hexane/ethyl acetate (19:1) as the eluent and, after subsequent distillation in a bulb-tube at about 50° C./15 mm Hg, gives 900 mg of pure colourless 2-chloro-2-methyl-3-butenenitrile. The degree of purity is about 99% according to GC.

Analytical data $^1$H-NMR (250 MHz, CDCl$_3$): 2.01 (s, 3 H), 5.38 (d, J=10 Hz, 1 H), 5.70 (d, J=16 Hz, 1 H), 5.96 (2 d, J$_1$=16, J$_2$=10, 1 H) ppm. IR (film): 2240 w, 1640 w, 1412 s, 1050 s, 943 s , 803 s; MS: 115 (M$^+$, 2), 100(14), 80(100), 53(90). Microanalysis: Calc.: C 51.97% H 5.23% N 12.12% Cl 30.68% Found: C 52.10% H 5.50% N 11.83% Cl 30.75%

EXAMPLE 2

Production of 2-chloro-2-methyl-3-butenenitrile (without using a catalyst)

102 g (1.1 mol) of 2-methyl-3-butenenitrile (purity about 84% according to GC) in 500 ml of n-hexane are placed in a 1 l double-jacketed flask equipped with a condenser, thermometer, thermostat and mechanical stirrer and the mixture is stirred and cooled to 10° C. 700 g of 13% Javelle water are then added portionwise to the resulting solution within about 20 minutes and the mixture is subsequently stirred for 7 hours at 10° C. (ice bath cooling). Thereafter, the mixture as well as rinsings ( 100 ml of n-hexane) are transferred into a Separating funnel and the organic phase is separated. The combined organic phases are finally washed with 100 ml of deionized water.

The thus-obtained hexane solution contains about 20–22 weight percent of 2-chloro-2-methyl-3-butenenitrile (yield about 89–92% according to GC) and can be used directly in the next process step (the alkanolysis).

EXAMPLE 3

Production of ethyl 2-chloro-2-methyl-3-butenoate from 2-methyl-3-butenenitrile via 2-chloro-2-methyl-3-butenenitrile (without isolating and purifying the intermediate—1st "through process" variant)

49.0 g (0.5 mol) of 2-methyl-3-butenenitrile (purity about 83%) in 250 ml of n-hexane are placed in a 1.5 l sulphonation flask equipped with a mechanical stirrer and a thermometer and the mixture is cooled (ice bath) to about 5° C. Thereto there are added in one portion while stirring 400 g (0.7 mol, 1.4 eq.) of fresh 13% Javelle water, which has been pre-cooled to about 5° C., followed by 2.8 g (26 mmol, about 5 mol %) of tetramethylammonium chloride. Then, the mixture is stirred at about +5° C. (ice bath) for about 16 hours and at room temperature for one and a half hours. Thereafter, the hexane phase is separated and the flask is rinsed with 50 ml of n-hexane, which at the same time is used to extract the aqueous phase again. The combined organic phase is now washed with 50 ml of water.

The resulting solution of crude 2-chloro-2-methyl-3-butenenitrile in n-hexane (about 300 ml) is now added dropwise while stirring at 5° C. within 30 minutes to a solution, previously prepared at 5° C., of 130 g (3.5 mol, 7 eq.) of gaseous hydrogen chloride in 200 ml of ethanol in a 1.5 l sulphonation flask equipped with a mechanical stirrer, a thermometer and a gas inlet tube. The reaction mixture is stirred at 0°–5° C. for about 16 hours and at room temperature for about 2–3 hours and then poured onto 300 g of ice and stirred for one hour. The aqueous phase is separated and extracted twice with 150 ml, a total of 300 ml, of n-hexane. The combined organic phase is washed with 100 ml of saturated sodium bicarbonate solution, dried with 30 g of anhydrous sodium sulphate and filtered, and the solvent (n-hexane) is distilled over a Raschig column (diameter: 2.5 cm; length: 30 cm) at normal pressure. The residue is distilled on a Vigreux column (NS 29.5; diameter: 2.5 cm; length: 20 cm) at 12 mbar. At a boiling point of 53°–57° C./12 mbar this gives 64.6 g (77.3% based on 2-methyl-3-butenenitrile) of ethyl 2-chloro-2-methyl-3-butenoate as a liquid which is as clear as water and which,has a purity according to GC of 97.2% (retention time: 7.8 minutes).

Analytical data $^1$H-NMR (250 MHz, CDCl$_3$): 1.31 (t, J=7 Hz, 3 H), 1.86 (s,3 H), 4.25 (q,J=7 Hz, 2 H), 5.27 (d, J=12 Hz, 1 H), 5.43 (d, J=16 Hz, 1 H), 6.21 (2 d, J$_1$=16 Hz, J$_2$=10, 1 H) ppm. IR (film): 1740 s, 1640 w, 1265 s, 1125 s, 991 m, 933 m; MS: 127 (M-Cl, 5),99(15),91(32),89(100),53(54). Microanalysis: Calc.: C 51.70% H 6.82% Cl 21.80% Found: C 51.68% H 6.96% Cl 21.90%

EXAMPLE 4

Production of ethyl 2-chloro-2-methyl-3-butenoate from 2-methyl-3-butenenitrile via 2-chloro-2-methyl-3-butenenitrile (without isolating and purifying the intermediate-2nd "through process" variant)

This variant is carried out as the 1st variant above, except that cyclohexane is used in place of n-hexane as the solvent and extraction agent.

With the analogous reaction of 49.0 g (0.5 mol) of 2-methyl-3-butenenitrile (purity about 83%) there are obtained at the end of the reaction sequence 63.0 g (75.3% based on 2-methyl-3-butenenitrile) of ethyl 2-chloro-2-methyl-3-butenoate as a colourless liquid which is as clear as water (b.p.: 55°–60° C./15 mbar; with a purity according to GC of 97.1%).

EXAMPLE 5

Production of ethyl 2-chloro-2-methyl-3-butenoate from 2-methyl-3-butenenitrile via 2-chloro-2-methyl-3-butenenitrile (without isolating and purifying the intermediate—3rd "through process" variant)

48 g (0.5 mol) of 2-methyl-3-butenenitrile (purity about 84.5%) in 250 ml of low-boiling petroleum ether are placed in a 1.5 l 4-necked sulphonation flask equipped with a mechanical stirrer and a thermostat. A suspension of 105 g (0.5 mol) of calcium hypochlorite in 250 ml of water is added thereto at 0° C. while stirring, followed by 5 g (24 mmol; 2.4 mol %) of tetraethylammonium bromide. The reaction mixture is stirred at 0° C. for 2 hours and at room temperature for a further 16 hours and a sample is analyzed by GC. This shows that the crude product consists, inter alia, of 41% of 2-chloro-2-methyl-3-butenenitrile and 37% of starting material.

Then, a further 50 g (0.25 mol) of calcium hypochlorite in 100 ml of water are added and the reaction mixture is stirred at room temperature for 24 hours and at 30° C. for 2 hours, which leads to a product containing 74.3% of 2-chloro-2-methyl-3-butenenitrile according to GC. The suspension is filtered and the filter material is washed with 150 ml of low-boiling petroleum ether. The organic phase is separated from the two-phase filtrate and is washed with 50 ml of water, dried over anhydrous sodium sulphate and filtered. The solvent is now distilled off over a Raschig column (diameter: 2.5 cm, length: 30 cm), at normal pressure until the sump weight is about 250 g. This solution is now diluted with 200 ml of diethyl ether and added dropwise within about 30 minutes while stirring at 5° C. to a previously prepared solution of 200 g (5.5 mol, 11 eq.) of gaseous hydrogen chloride in 200 ml of absolute ethanol. The mixture is stirred at 5° C. for about 16 hours, then at room temperature for one hour. A sample of the mixture has an 84.6% ethyl 2-chloro-2-methyl-3-butenoate content. For the working up, the mixture is poured onto 500 g of ice, stirred at room temperature for one hour and treated with 100 g of solid sodium chloride. The organic phase is separated and the aqueous phase is extracted three times with 250 ml, a total of 750 ml, of diethyl ether. The combined ether phases are washed once with 100 ml of saturated sodium bicarbonate solution, dried over anhydrous sodium sulphate, filtered and concentrated. Subsequent distillation on a Vigreux column (diameter 2.5 cm, length 30 cm) gives, at 54°–58° C./14 mbar, 51.0 g (60%) of ethyl 2-chloro-2-methyl-3-butenoate as a colourless liquid having a purity of 95.1% according to GC.

EXAMPLE 6

Manufacture of (3-ethoxycarbonyl-2-butenyl) triphenylphosphonium chloride from ethyl 2-chloro-2-methyl-3-butenoate 84.0 g (0.48 mol, GC-corrected) of ethyl 2-chloro-2-methyl-3-butenoate (purity 93% according to GC) and 144 g (0.55 mol) of triphenylphosphine are dissolved in 1 l of toluene in a 2.5 l four-necked sulphonation flask equipped with a mechanical stirrer, thermometer and condenser and heated under reflux for 48 hours (seeding with already prepared phosphonium salt is carried out when the mixture is at about 100° C.). After cooling to room temperature the crystal slurry is filtered, washed three times with 300 ml of toluene, a total of 900 ml of toluene, and dried in a drying oven at 50° for 20 hours under a water-jet vacuum. This gives 187.8 g (88%) of (3-ethoxycarbonyl-2-butenyl) triphenylphosphonium chloride as a light beige powder with a m.p. of 191°–192° C. and a purity of 95.7% according to HPLC.

EXAMPLE 7

Manufacture of (3-ethoxycarbonyl-2-butenyl triphenylphosphonium chloride from 2-methyl-3-butenenitrile via 2-chloro-2-methyl-3-butenenitrile and ethyl 2-chloro-2-methyl-3-butenoate (without isolating and purifying the two intermediates—4th "through process" variant).

51 g (0.5 mol) of 2-methyl-3-butenenitrile (purity about 80%) in 250 ml of n-hexane are placed in a 1.5 l four-necked sulphonation flast equipped with a mechanical stirrer and a thermometer and the mixture is cooled to about 5° C. (cryostat). Then, 350 g (0.63 mol, 1.25 eq.) of fresh 13% Javelle water are added dropwise at 5° C. within about 20 minutes while stirring and 1.4 g ( 13 mmol, 2.5 mol %) of tetramethylammonium chloride are subsequently added. After stirring at 5° C. (cryostat) for 16 hours the hexane phase is separated and the flask is rinsed with 50 ml of n-hexane, which is used to extract the aqueous phase again. The combined organic phase is finally washed with 50 ml of water.

This solution of crude 2-chloro-2-methyl-3-butenonitrile in n-hexane (not dried, about 300 ml) is now added dropwise at 10° C. within about 30 minutes while stirring to a previously prepared solution of 100 g (2.75 mol, 5.5 eq.) of gaseous hydrogen chloride in 200 ml of absolute ethanol in a 1.5 l four-necked sulphonation flask equipped with a mechanical stirrer, a thermometer and a gas inlet tube. The resulting mixture is stirred at 15° C. (cryostat) for 16 hours and thereafter cooled. 300 g of ice are added to the solution and it is then stirred at room temperature for about 30 minutes. The aqueous phase is separated and extracted twice with 75 ml, a total of 150 ml, of n-hexane. The combined organic phase is washed with 75 ml of saturated sodium bicarbonate solution and subsequently (without drying) the n-hexane is distilled off using a Raschig column (30×2.5 cm) at normal pressure. This gives a yellow residue (92.6 g) which is dissolved in 1 l of toluene. 131 g (0.5 mol) of triphenylphosphine are added to the solution in a 2.5 l four-necked sulphonation flask which is equipped with a mechanical stirrer and a thermometer. The mixture is subsequently heated under reflux for 40 hours (seeding with already prepared phosphonium salt is carried out after about 30 minutes). The separated crystal slurry is cooled to 20° C., filtered off under suction, washed three times with 250 ml, a total of 750 ml, of toluene and dried in a vacuum drying oven at about 50° C. for 16 hours. This gives 162.8 g (74.4% based on 2-methyl-3-butenenitrile) of beige (3-ethoxycarbonyl-2-butenyl) triphenylphosphonium chloride with m.p. 191° C. and a purity of 97.1% according to HPLC.

EXAMPLE 8

Manufacture of (3-cyano-2-butenyl) triphenylphosphonium chloride from 2-methyl-3-butenenitrile via 2-chloro-2-methyl-3-butenenitrile (without isolating and purifying the intermediate— "through process")

49 g (0.5 mol) of 2-methyl-3-butenenitrile (purity 84% according to GC) are placed in 250 ml of toluene and the mixture is cooled to 5° C. 350 g of 13% Javelle water (0.63 mol) are added dropwise thereto within 30 minutes and 1.4 g of tetramethylammonium chloride are subsequently added. The resulting two-phase mixture is stirred at 0°–5° C. for 16 hours and at room temperature for a further 3 hours. Then the aqueous phase is separated and extracted with 100 ml of toluene. The combined organic phases are washed with 50 ml of water, dried over anhydrous sodium sulphate and filtered. This gives 500 g of a solution of crude 2-chloro-2-methyl-3-butenenitrile in toluene.

An additional 200 ml of toluene are added to 250 g of this toluene solution. After the addition of 70 g (about 0.26 mol) of triphenylphosphine the yellowish solution is heated to 90° C. (a precipitate begins to form after 10 minutes). Then the mixture is stirred at 100° C. for 16 hours. The mixture is subsequently cooled to 5° C. and the precipitate is filtered off, washed three times with 150 ml, a total of 450 ml, of toluene and dried at 50° C. in a water-jet vacuum for 4 hours. This gives 79.0 g (80.3%, corrected) of (E/Z)-(3-cyano-2-butenyl)triphenylphosphonium chloride as an almost white powder with m.p. 277°–278° C.; HPLC: purity 96%; (E/Z) mixture (E/Z ratio about 1:1).

Microanalysis: Calc.: C 73.11% H 5.60% N 3.71% Cl 9.38% Found: C 72.99% H 5.49% N 3.43% Cl 9.66%

EXAMPLE 9

Manufacture of (3-ethoxycarbonyl-2-butenyl) triphenylphosphonium ethyl sulphate from (3-cyano-2-butenyl)triphenylphosphonium chloride 20.0 g (0.05 1 mol) of (E/Z)-(3-cyano-2-butenyl) triphenylphosphonium chloride [E/Z ratio about 5:1 according to $^1$H-NMR(CDCl$_3$); purity about 97.4% according to HPLC] and 54 ml/42.7 g (0.92 mol) of ethanol are placed under argon in a 350 ml four-necked sulphonation flask equipped with a mechanical stirrer, a condenser, a thermometer and a dropping funnel. 26 ml/47.5 g (0.46 mol) of concentrated sulphuric acid (purity 95–97% according to GC) are added dropwise within 20 minutes to the resulting suspension under argon while cooling with acetone/ice and while stirring (500 r/minute) in such a manner that the temperature is held at 3° to 5° C. The viscous, colourless solution is stirred under reflux for 20 hours (oil bath temperature: 100° C.). The initial internal temperature of 92° C. gradually falls to 83° C. After cooling in an ice bath the reaction mixture is suction filtered and the filter material is washed three times with 50 ml, a total of 150 ml, of methylene chloride. Ammonium, chloride and sulphate ions are detected in the colourless precipitate (mineral salt). The filtrate is washed neutral five times with 40 ml, a total of 200 ml, of water. The organic phase is dried over anhydrous sodium sulphate, filtered and evaporated in a 1 l round flask at 35° C. under a water-jet vacuum in a rotary evaporator. This gives 26.9 g of crude (E)-(3-ethoxycarbonyl-2-butenyl) triphenylphosphonium ethyl sulphate as a pale yellow foam which has a purity of 88.4% according to HPLC.

In order to purify the product, the foam (26.9 g) is dissolved in 60 ml of hot acetone. The product crystallizes from the solution which is initially cooled in an ice bath. In order to complete the crystallization, 150 ml of diethyl ether are added after 30 minutes and the solution is stirred in an ice bath for a further one hour. The resulting crystallizate is filtered off under suction, washed twice with 25 ml, a total of 50 ml, of diethyl ether and dried over phosphorus pentoxide at 22 mbar for 16 hours. This gives 22.8 g of (E)-(3-ethoxycarbonyl-2-butenyl)triphenylphosphonium ethyl sulphate [82% based on (3-cyano-2-butenyl) triphenylphosphonium chloride] as a colourless powder, m.p. 121°–122° C.; HPLC: purity 94.4%; thin-layer chromatography: $R_f$=0.45 with eluent ethyl acetate:acetone:formic acid 8:1:1 and iodine as the developer.

One recrystallization from 60 ml of acetone and 150 ml of diethyl ether as described above gives 21.9 g of product (79% based on the starting material) as a colourless powder, m.p. 123°–125° C; HPLC: purity 95.52%.

EXAMPLE 10

Production of (l,u)-3,4-dichloro-2-methyl-butanenitrile from 2-methyl-3-butenenitrile A solution of 39.6 g (0.4 mol, 1 eq.) of 2-methyl-3-butenenitrile in 5.6 g (0.071 mol, 0.18 eq.) of pyridine (purity 99.8% according to GC) is placed under argon in a 200 ml four-necked sulphonation flask equipped with a mechanical stirrer, a thermometer and a gas inlet tube. About 34 g (0.48 mol, 1.2 eq.) of chlorine (purity 99.9% according to GC, dried over concentrated sulphuric acid) are introduced under argon while cooling (acetone/ice bath) within 34 minutes at a throughflow rate of 1 g/min (adjustment with a rotameter). The amount of chlorine taken up is controlled by weighing the flask. The temperature rises from about −10° C. to 20° C. A colourless precipitate (pyridinium hydrochloride) forms first and gradually changes into an oily clump. The reaction mixture is poured into 20 ml of water. The reaction flask is rinsed twice with 25 ml, a total of 50 ml, of water. The organic phase is washed four times with 25 ml, a total of 100 ml, of water, dried over anhydrous sodium sulphate and filtered. Each aqueous phase is extracted with 25 ml, a total (4 wash phases) of 100 ml, of n-pentane. The pentane phases are washed neutral twice with 25 ml, a total of 50 ml, of water, dried over anhydrous sodium sulphate and filtered. The entire organic phase is evaporated at about 15° C. under a water-jet vacuum (rotary evaporator fitted with a Dewar condenser filled with dry ice/acetone). This gives 60 g of crude (l,u)-3,4-dichloro-2-methyl-butanenitrile as a colourless oil: GC (l+u)=91.9%; diastereomer ratio (l): (u) about 1:1.

Distillation over a Vigreux column (5 cm) gives 52.3 g (74%) of (l,u) product which is about 90% pure according to GC and which has a (l)/(u) ratio of about 1:1.

EXAMPLE 11

Production of 4-chloro-2-methyl-2-butenenitrile from 3,4-dichloro-2-methylbutanenitrile 24.0 g (0.15 mol) of (l,u)-3,4-dichloro-2-methylbutanenitrile [(l)+(u)=94.5%, according to GC; diastereomer ratio (l):(u)=1:1, according to GC and $^1$H-NMR), 450 ml of n-pentane and 150 ml (0.3 mol) of 2N sodium hydroxide solution are placed under argon in a 1 l round flask equipped with a magnetic stirrer. The mixture is stirred under argon at room temperature for 2 hours. The pentane solution is washed to neutrality four times with 50 ml, a total of 200 ml, of water, dried over anhydrous sodium sulphate, filtered and evaporated in a rotary evaporator (bath temperature about 15° C., acetone/dry ice cooling). This gives 18.5 g of crude (E/Z)-4-chloro-2-methyl-2-butenenitrile as a colourless oil which is subsequently distilled over a 10 cm long silvered Vigreux column. This leads to 15.6 g (88% based on 3,4-dichloro-2-methylbutanenitrile) of (E/Z)-4-chloro-2-methyl-2-butenenitrile as a colourless lacrimatory oil which is damaging to the skin, b-p.$_{0.1}$=20°–21° C.; 98% pure (E+Z) according to GC; (E)/(Z) ratio about 1:1.25.

EXAMPLE 12

Manufacture of (3-cyano-2-butenyl) triphenylphosphonium chloride as an (E/Z) mixture from (E/Z)-4-chloro-2-methyl-2-butenenitrile 1.15 g (10 mmol) of (E/Z)-4-chloro-2-methyl-2-butene (E:Z=1:1), 2.62 g (10 mmol) of triphenylphosphine and 7 ml of isopropanol are placed under argon in a 25 ml round flask equipped with a magnetic stirrer. The reaction mixture is stirred under argon at room temperature for 60 hours. After a reaction period of 30 minutes the colourless suspension passes into solution within about 2 minutes. Product then gradually separates out. Subsequently, 15 ml of ethyl acetate are added at room temperature. The crystallizate is filtered off with the addition of further 5 ml of ethyl acetate, then washed twice with 5 ml, a total of 10 ml, of diethyl ether and dried in a desiccator for 16 hours over anhydrous phosphorus pentoxide at 22 mbar. This gives 3.1 g (79%) of (E/Z)-(3-cyano-2-butenyl)triphenylphosphonium chloride as a colourless crystalline powder, m.p. 276°–277° C.; about 95.8% (E)+(Z) pure according to HPLC; (E)/(Z) ratio about 5:1.

We claim:

1. A process for producing a Wittig ester salt of the formula:

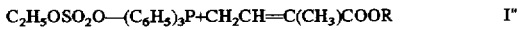
$$C_2H_5OSO_2O\text{—}(C_6H_5)_3P^+CH_2CH\!=\!C(CH_3)COOR \qquad I''$$

wherein R is $C_{1-4}$-alkyl, which process comprises reacting a compound of the formula:

$$Cl(C_6H_5)_3P^+CH_2CH\!=\!C(CH_3)CN \qquad V$$

with a mixture of an alkanol, ROH, wherein R is as in formula I'', and concentrated sulphuric acid to obtain said Wittig ester salt.

2. The process of claim 1 wherein the alkanol is methanol or ethanol.

3. The process of claim 2 wherein the concentrated sulfuric acid is 95–97% by weight sulfuric acid and 3–5% by weight water.

4. The process of claim 3 wherein the molar ratio of alkanol to sulphuric acid is from about 1:1 to about 3:1.

5. The process of claim 4 wherein the molar ration of alkanol to sulphuric acid is about 2:1.

6. The process of claim 5 wherein the alkanol is ethanol.

* * * * *